United States Patent

Ling et al.

[11] Patent Number: 5,807,851
[45] Date of Patent: Sep. 15, 1998

[54] 2,3-BENZODIAZEPINE DERIVATIVES AS NON-COMPETITIVE AMPA

[75] Inventors: István Ling; Gizella Ábrahám; Pál Berzsenyi; István Tarnawa; Sándor Sólyom; Ferenc Andrási; Tamás Hámori; Emese Csúzdi; Katalin Horváth; Melinda Gál; Imre Moravcsik; Márta Szollosy, all of Budapest, Hungary

[73] Assignee: Egis Gyogyszergyar Rt., Budapest, Hungary

[21] Appl. No.: 832,777

[22] Filed: Apr. 4, 1997

[51] Int. Cl.$^6$ .......................... A01N 43/62; C07D 243/00
[52] U.S. Cl. ............................................ 514/221; 540/567
[58] Field of Search .............................. 540/567; 514/221

[56] References Cited

U.S. PATENT DOCUMENTS 5,288,863  2/1994  Somogyi et al. ..................... 540/567

OTHER PUBLICATIONS

Gatta et al., "Derivatives of 2,3–benzodiazepine", IL Farmaco, Vol. XL (Dec. 1985), No. 12, pp. 942–955.

Primary Examiner—Mukund J. Sham
Assistant Examiner—Tamthom T. Ngo
Attorney, Agent, or Firm—Beveridge, DeGrandi. Weilacher & Young, L.L.P.

[57] ABSTRACT

Derivatives of 2,3-benzodiazepine are substituted by one or two halogen atom(s) and have the general formula

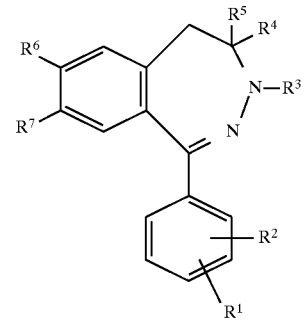

These derivatives are non-competitive AMPA antagonists and are used in pharmaceutical compositions. A process to make the 2,3-benzodiazepine derivatives includes converting starting compounds which are substituted by one or two halogen groups and have the general formula

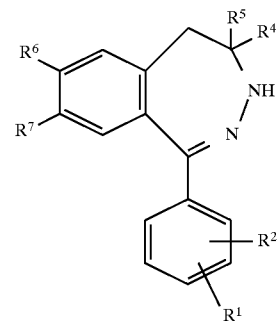

12 Claims, 1 Drawing Sheet

2,3-BENZODIAZEPINE DERIVATIVES AS NON-COMPETITIVE AMPA

The invention refers to novel 2,3-benzodiazepines substituted by one or two halo atom(s) and pharmaceutical compositions containing the same.

Several biologically active and therapeutically useful 2,3-benzodiazepines are known, wherein the benzo ring is substituted by two methoxy groups or a methylenedioxy group. 7,8-Dimethoxy derivatives are described e.g. in HU-P Nos. 155 572, 179 018, 191 702 and 195 788. These compounds have, in the first place, anxiolytic and/or antidepressant as well as positive inotropic activity. Compounds having a methylenedioxy substituent in the same positions of the benzo ring are known from e.g. HU-P Nos. 191 698, 191 702 and 206 719 as well as U.S. Pat. No. 5,459,137. In contrast to the dimethoxy-2,3-benzodiazepines, the methylenedioxy compounds are characterized, principally, by their spasm inhibiting, muscle relaxant and neuroprotective activity.

From the literature it is known that the latter compounds exert their activity through the non-competitive inhibition of the AMPA receptor. (See among others: S. D. Donevan et al., Neuron, 10, 51–59 (1993); S. D. Donevan et al.; J. Pharmacol. Exp. Ther., 271, 25–29 (1994); as well as I. Tarnawa et al., Bioorg. Med. Chem. Lett., 3, 99–104 (1993).

Furthermore, it is known that, in the central nervous system of mammals, L-glutamic acid is the most important neurotransmitter of excitatory action. Under pathological circumstances, the concentration of glutamic acid rises abnormally in the space outside the cell leading to an acute or chronic damage of the cells of the central nervous system.

The exciting amino acids such as glutamic acid exert their action by activating the iontropic (i.e. ionic channel) receptors as well as the metabotropic receptors that bind to proteins G. The types of the ionotropic glutamate receptors are designated according to the agonists suitable for the selective excitation thereof. Thus, the receptors NMDA, AMPA and kainate (earlier called quisqualate) are distinguished, and within each receptor type further subtypes exist /Ann. Rev. Neurosci., 17, 31 (1994)/.

It was shown that glutamate receptors of AMPA type play an important part in numerous acute and chronic diseases affecting the central nervous system such as epilepsy, diseases accompanied by muscle spasticity and various neurodegenerative diseases, thus, by inhibiting the AMPA receptors, spasm inhibiting, muscle relaxant and neuroprotective effect can be obtained. /See among others: Cerebrovasc. Brain Metab. Rev., 6, 225 (1994); Neurology, 44 Suppl. 8, S14 (1994); J. Pharmacol. Exp. Ther., 260, 742 (1992)./

Activation of the AMPA receptors can be inhibited by means of competitive and non-competitive antagonists. In contrast to competitive antagonists, the use of the non-competitive antagonists can be preferable, in general, since a higher protection is obtained at an extreme high endogenous concentration of the exciting amino acid /Epilepsy Res., 15, 179 (1993)/.

Based on the above facts, it was an invention of especially significance that 2,3-benzodiazepines substituted by a methylenedioxy group have, due to their non-competitive AMPA antagonistic activity, spasm inhibiting, muscle relaxant as well as neuroprotective effect, thus, the compounds can be used in the therapy as antispasmodics, antiepileptics, furthermore in acute and chronic neurodegenerative diseases and potentially in any diseases wherein the inhibition of the exciting amino acid is desirable at the receptor level.

Surprisingly, it was found that the therapeutically valuable non-competitive AMPA receptor antagonistic activity is remarkably retained if the benzo ring contains, instead of the methylenedioxy group, one or two chloro or bromo atom(s). Furthermore, it was found that the novel halo compounds have more favourable properties than the known ones.

This observation is surprising since it was believed that the presence of the methylenedioxy group is an essential condition to obtain the above activities.

BRIEF DESCRIPTION OF DRAWINGS

Thus, the invention refers to novel 2,3-benzodiazepines of the formula I (FIG. I), wherein $R^1$ and $R^2$ represent, independently, a hydrogen, a halo, a $C_{1-4}$ alkyl group, a $C_{1-4}$ alkoxy group, a nitro group, a trifluoromethyl group of a group of the formula —$NR^8R^9$, wherein $R^8$ and $R^9$ stand, independently, for a hydrogen, a $C_{1-4}$ alkyl group or a group of the formula —$COR^{10}$, wherein $R^{10}$ is a hydrogen, a $C_{1-6}$ alkyl group that can be substituted, a $C_{6-10}$ aryl group, a $C_{1-4}$ alkoxy group, a $C_{3-5}$ cycloalkyl group, a $C_{2-6}$ alkenyl group, a $C_{3-5}$ cycloalkoxy group or a group of the formula —$NR^{11}R^{12}$, wherein $R^{11}$ and $R^{12}$ means, independently, a hydrogen, a $C_{1-4}$ alkyl group, a $C_{3-5}$ cycloalkyl group or a $C_{6-10}$ aryl group, $R^3$ represents a $C_{1-4}$ alkyl group, a $C_{3-5}$ cycloalkyl group or a group of the formula —CO—$R^{13}$, wherein $R^{13}$ has the same definitions given in relation to $R^{10}$, $R^4$ and $R^5$ means, independently, a hydrogen or a $C_{1-3}$ alkyl group, $R^6$ and $R^7$ are, independently, a hydrogen, a chloro or a bromo, with the provision that if one of $R^6$ and $R^7$ stands for a hydrogen, the other is different from hydrogen, as well as the isomers and the acid addition salts thereof.

In the definitions given in connection with formula I, the alkyl and alkylene group is a straight or branched chain group. If the alkyl group is substituted, the substituent is an alkoxy group or a halo. The cycloalkyl group is a cyclopropyl, cyclobutyl or cyclopentyl group. The aryl group is a phenyl or a naphthyl group.

Figure 1:
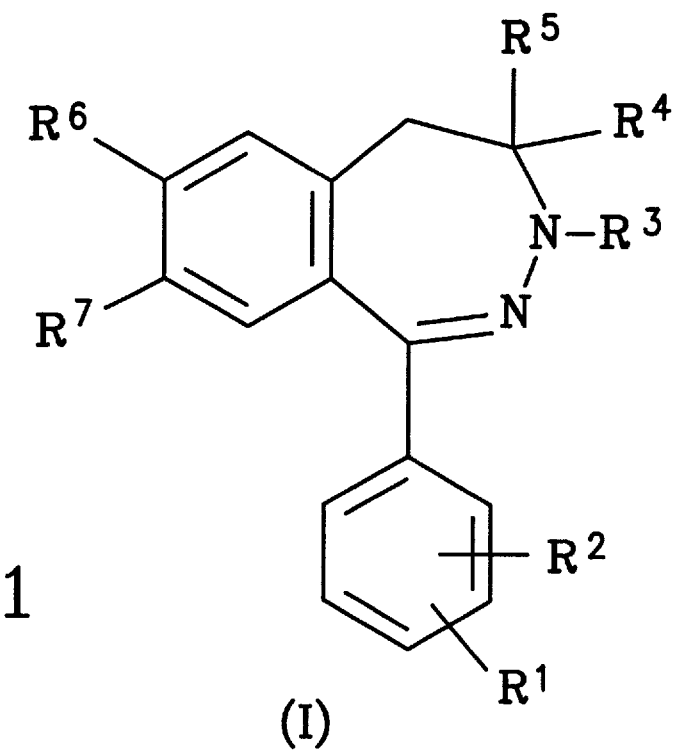
Figure 2:
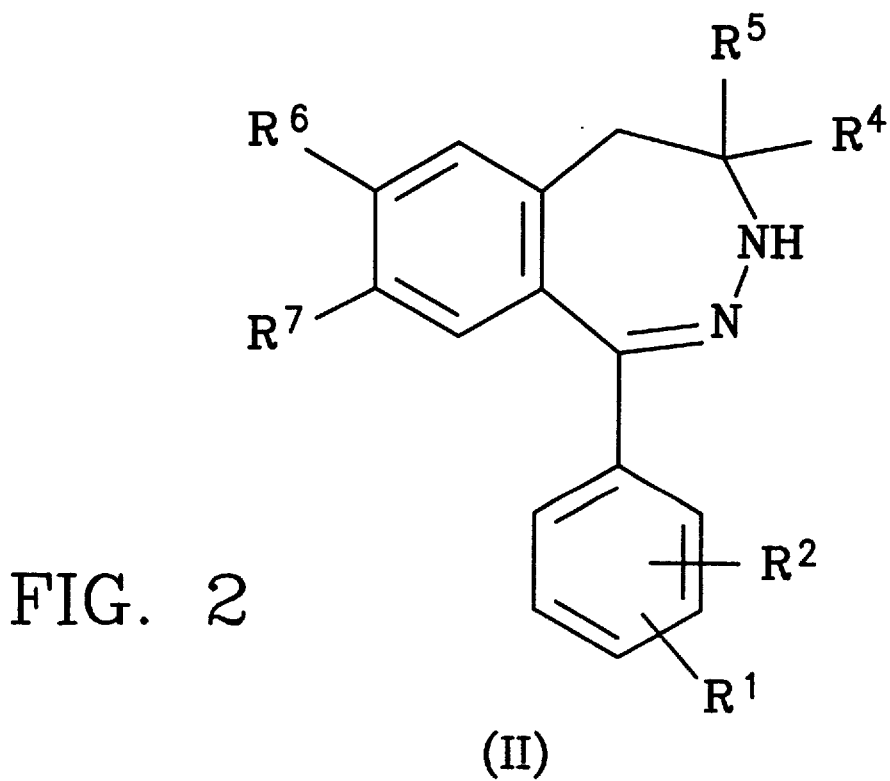

Since the compounds of the formula I contain a chiral centre, under the isomers of the compounds of the formula I both enantiomers and in case of certain substitutions the stereoisomers E and Z as well as diastereomers, tautomers and mixtures thereof such as racemates are meant.

The acid addition salts of the compounds of the formula I are salts formed with physiologically suitable inorganic or organic acids. A suitable inorganic acid is e.g. hydrochloric acid, hydrogen bromide, phosphoric acid or sulfuric acid. The organic acid is e.g. formic acid, acetic acid, maleic acid, fumaric acid, malic acid, lactic acid, tartaric acid, citric acid or methanesulfonic acid.

A preferred subgroup of the compounds of the invention consists of the compounds of the formula I, wherein $R^1$ represents an amino group in position 4, $R^2$, $R^4$ and $R^6$ stand for hydrogen, $R^5$ means a methyl group, $R^7$ is a halo and $R^3$ represents an aliphatic acyl group or an alkylcarbamoyl group.

Within this preferred subgroup, especially preferred species consist of the compounds wherein $R^3$ stands for an acetyl group, a propionyl group, a cyclopropylcarbonyl group or a methylcarbamoyl group.

The compounds of the invention can be prepared from the corresponding starting compounds of the formula II (FIG. II), wherein $R^1$, $R^2$, $R^4$, $R^5$, $R^6$ and $R^7$ are as defined above, by the analogy of the processes given in HU-P No. 206 719 or U.S. Pat. No. 5,459,137. The Examples given below show only one possibility for the preparation of the compounds of the formula I.

In the preferred preparation of the compounds of the invention, the usual methods of 2,3-benzodiazepine syntheses are employed. Thus, amino groups are alkylated with an alkyl halide or reductive amination with an oxo compound is used. Acylation is performed, in general, with an acid chloride, anhydride, mixed anhydride or alkyl or phenyl chlorocarbonate—in case of catalysis with an acid binding agent and/or pyridine derivative at room temperature—or at higher temperatures in a solvent.

Carbamoyl groups are formed by a reaction with the corresponding isocyanate. However, it is also possible to acylate with an active ester such as phenyl chlorocarbonate, and to react the compound obtained with a primary or secondary amino compound.

The nitro group is reduced, in general, catalytically, in the presence of a Raney nickel, palladium or platinum catalyst. In addition to hydrogen gas, hydrazine hydrate or for example ammonium formate can be also used as the hydrogen source.

The starting compounds of the formula II are novel, thus, the invention refers to these compounds, too. They are prepared according to the process described in HU-P No. 191 702 or by the analogy of the preparation of known compounds. Details of the process are shown in the Examples.

As stated above, the compounds of the invention have a significant non-competitive AMPA antagonistic activity, thus, they can be used in the therapy as antispasmodics, muscle relaxant as well as for neuroprotection, furthermore in the treatment of other neurological and psychiatrical disorders that can be attributed to an increased excitation state of the AMPA receptor.

The compounds of the formula I can be transformed into pharmaceutical compositions that can be administered enterally or parenterally. For this purpose, conventional organic or inorganic carriers or excipients of the pharmaceutical industry such as water, gelatin, arabic gum, lactose, starch, magnesium stearate, talc, vegetable oils, poly(ethylene glycol) etc. can be used.

The pharmaceutical composition can be a solid dosage form such as a tablet, dragée, suppository or capsule, or can be prepared as a liquid dosage form such as a solution, suspension or emulsion. In addition to the carriers and excipients mentioned above, further additives having preserving, stabilizing, emulsifying, buffering etc. effects can be employed.

For parenteral administration, the dosage form consists of a sterile solution or suspension of the active ingredient. In this case, the sterile vehicle may contain one or more adjuvant(s) e.g. a local anesthetic, a stabilizing agent or a buffer.

The dosage administered to a patient depends on the method of administration, the kind and severity of disease as well as the weight and age of the patient. The daily dose is 0.5 to 1000 mg, preferably 20 to 200 mg, and can be administered in one portion or in more portions.

The AMPA antagonistic activity of the compounds of the formula I is shown by the following test.

Antagonizing the effect of kainate (in vitro test)

The in vitro activity of the compounds was determined on isolated chicken retina preparations /M. J. Sheardown, Brain Res., 607, 189 (1993)/. The spreading depression was developped with 5 microM of kainate (the chemical name of kainic acid is 2-carboxy-4-isopropenyl-3-pyrrolidine-acetic acid), and the $IC_{50}$ values were determined according to Sheardown. The compounds were tested in at least 3 concentrations. Compounds having AMPA antagonistic activity inhibit the response to the kainate having AMPA receptor agonistic activity, and the inhibition obtained depends on the concentration of the compounds. The $IC_{50}$ values are shown in Table 1.

TABLE 1

| In vitro kainate antagonistic activity | |
|---|---|
| Compound (No. of Example) | In vitro retinal spreading depression $IC_{50}$ in microM |
| 2 | 3.2 |
| 4 | 3.6 |
| 6 | 8.2 |
| 8 | 4.6 |
| 10 | 2.5 |
| 12 | 1.2 |
| A | 9.5 |

Reference compound: A:
5-(4-aminophenyl)-9H-1,3-dioxolo/4,5-h//2,3/benzodiazepine (GYKI 52 466; HU-P No. 191 698, Example 8).

The compounds of the present invention and the process for the preparation thereof are further elucidated by means of the following Examples, without restricting the scope of the invention.

EXAMPLE 1

3-Acetyl-7-chloro-4-methyl-1-(4-nitrophenyl)-4,5-dihydro-3H-2,3-benzodiazepine 0.72 g (2.2 mmoles) of 7-chloro-4-methyl-1-(4-nitrophenyl)-4,5-dihydro-3H-2,3-benzodiazepine are stirred in 4 ml of acetic anhydride at 25° C. for 3 hours, then the reaction mixture is poured onto 20 ml of ice water, the crystalline product is filtered and washed with water several times. The crude product obtained is purified by suspending it in 4 ml of hot ethanol. After filtration and drying, 0.69 g (88%) of the title compound are obtained M.p.: 174°–175° C.

The starting compound of Example 1 is prepared as follows:

Step A
6-Chloro-3-methyl-1-(4-nitrophenyl)isochroman

To a solution of 17.06 g (100 mmoles) of 1-(3-chlorophenyl)-2-propanol /prepared by an analogous process of the one described in J. Med. Chem., 21, 454 (1978)/ and 15.11 g (100 mmoles) of 4-nitrobenzaldehyde in 100 ml of anhydrous benzene, 13.65 g (100 mmoles) of zinc chloride are added (the zinc chloride was ignited before the addition), and anhydrous hydrogen chloride gas is led into the reaction mixture for 3 hours.

The mixture is boiled for 2,5 hours, and, after cooling, admixed to 100 ml of water. The organic phase is separated, washed with water, aqueous sodium hydrogen carbonate solution, then with saturated aqueous sodium chloride solution, dried and evaporated. The residual 30.95 g of crude oily product are crystallized from 200 ml of hot ethanol to obtain 23.49 g (77%) of the title compound. M.p.: 118°–120° C.

Step B
6-Chloro-3-methyl-1-(4-nitrophenyl)-2-benzopyrilium perchlorate 26.9 g (88.5 mmoles) of the isochroman derivative prepared in Step A are dissolved in 270 ml of acetone, and to the solution obtained, 116 ml (310 mmoles) of Jones' reagent are added, drop by drop, under ice cooling in 1 hour, then the reaction mixture is stirred at 25° C. for 4 hours. The salt of chrom separated during the reaction is filtered, and the filtrate is evaporated.

The residual crystals are suspended in 100 ml of water, then filtered again. The crystals are dissolved in 304 ml of hot glacial acetic acid, 5.91 ml of 70% perchloric acid are added, then, after cooling, the crystals separated are filtered and washed 4 times using 10 ml of glacial acetic acid each time.

Thus, 6.84 g (19%) of the title compound are obtained. M.p.: 236°–237° C. (decomp.).

Step C
7-Chloro-4-methyl-1-(4-nitrophenyl)-5H-2,3-benzodiazepine 6.43 g (16 mmoles) of the benzopyrilium perchlorate prepared in Step B are dissolved in 32 ml of dimethylformamide, and to the solution obtained, 2.31 ml (48 mmoles) of 98% hydrazine hydrate are added, drop by drop, and the reaction mixture is stirred at 25° C. for 1 hour. The mixture is poured into 320 ml of water, the product separated is filtered and washed 5 times using 10 ml of water each time. The crude product is purified by suspending it in 50 ml of hot ethanol. Thus, 4.41 g (87%) of the title compound are obtained. M.p.: 227°–228° C.

Step D
7-Chloro-4-methyl-1-(4-nitrophenyl)-4,5-dihydro-3H-2,3-benzodiazepine 1.5 g (4.78 mmoles) of the benzodiazepine derivative prepared in Step C are suspended in 60 ml of methanol, and to the suspension obtained, 4.64 g (57.3 mmoles) of concentrated hydrochloric acid are added, then, under cold water cooling, 2.07 g (54.8 mmoles) of sodium borohydride are added in portions. The suspension is stirred at 25° C. for 1 hour, then solid sodium carbonate is added to adjust the pH of the mixture to a value of about 8. The mixture is diluted with 60 ml of water, the product separated is filtered, washed 4 times using 5 ml of 50% aqueous methanol each time, and dried to obtain 1.47 g (97.4%) of the title compound. M.p.: 152°–154° C.

EXAMPLE 2

3-Acetyl-1-(4-aminophenyl)-7-chloro-4-methyl-4,5-dihdyro-3H-2,3-benzodiazepine 0.66 g (1.8 mmoles) of 3-acetyl-7-chloro-4-methyl-1-(4-nitrophenyl)-4,5-dihydro-3H-2,3-benzodiazepine (prepared in Example 1) are suspended in 35 ml of methanol, then about 0.5 g of wet Raney nickel catalyst, and, under vigorous stirring, 0.32 ml (6.5 mmoles) of 98% hydrazine hydrate are added. The reaction mixture is stirred for further 45 minutes, then the catalyst is removed by filtration, washed with methanol, the combined filtrates are evaporated, and the residue is treated with 10 ml of water to obtain a solid product. The 0.54 g of crude product are recrystallized from 2 ml of ethanol to give 0.44 g (75%) of the title compound. M.p.: 90°–92° C.

EXAMPLE 3

7-Chloro-4-methyl-3-(methylcarbamoyl)-1-(4-nitrophenyl)-4,5-dihydro-3H-2,3-benzodiazepine 0.72 g (2.2 mmoles) of 7-chloro-4-methyl-1-(4-nitrophenyl)-4,5-dihydro-3H-2,3-benzodiazepine prepared in Example 1, Step D are dissolved in 15 ml of anhydrous dichloromethane, and to the solution obtained, 1.3 ml (22.0 moles) of methyl isocyanate are added, and the reaction mixture is left to stand at 25° C. for 10 days. The mixture is evaporated, and the residue is recrystallized from 3 ml of hot ethanol. The crystals are filtered, washed 3 times using 1 ml of ethanol each time, then dried. Thus, 0.78 g (95%) of the title compound are obtained. M.p.: 224°–226° C.

EXAMPLE 4

1-(4-Aminophenyl)-7-chloro-4-methyl-3-(methylcarbamoyl)-4,5-dihydro-3H-2,3-benzodiazepine 0.75 g (2.0 moles) of 7-chloro-4-methyl-3-(methylcarbamoyl)-1-(4-nitrophenyl)-4,5-dihydro-3H-2,3-benzodiazepine prepared as described in Example 3 are reduced according to the method of Example 2, and the crude product obtained is recrystallized from hot ethanol. Thus, 0.55 g (80%) of the title compound are obtained. M.p.: 134°–136° C.

EXAMPLE 5

3-Acetyl-8-chloro-1-(4-nitrophenyl)-4,5-dihydro-3H-2,3-benzodiazepine 0.69 g (2.19 mmoles) of 8-chloro-4-methyl-1-(4-nitrophenyl)-4,5-dihydro-3H-2,3-benzodiazepine are acetylated by the method described in Example 1. 0.70 g (89%) of the title compound are obtained. M.p.: 227°–229° C.

The starting compound of Example 5 is prepared as follows:

Step A
7-Chloro-3-methyl-1-(4-nitrophenyl)-isochroman

Example 1, Stage A is reacted with the exception that the starting compound consists of 11.94 g (70 mmoles) of 1-(4-chlorophenyl)-2-propanol /J. Med. Chem., 21, 454 (1978)/ and the reaction mixture is boiled for 1.5 hours. Thus, 6.8 g (32%) of the title compound are obtained. M.p.: 120°–123° C.

Step B
7-Chloro-3-methyl-1-(4-nitrophenyl)-2-benzopyrilium perchlorate 6.8 g (22.4 mmoles) of the isochroman derivative obtained in Step A are oxidized by the method of Example 1, Step B with the Jones' reagent. The salt is prepared in glacial acetic acid using perchloric acid. Thus, 3.73 g (42%) of the title compound are obtained. M.p.: 247°–255° C.

Step C
8-Chloro-4-methyl-1-(4-nitrophenyl)-5H-2,3-benzodiazepine 4.1 g (10.25 mmoles) of the benzopyrilium perchlorate obtained in Step B are added to a mixture of 20.5 ml of dimethylformamide and 1.5 ml (70.7 mmoles) of 98% hydrazine hydrate under cooling with cold water. The reaction mixture is stirred at 25° C. for 1.5 hours, then 25 ml of water are added, the crude product separated is filtered, washed 4 times using 5 ml of water each time, then recrystallized from 25 ml of isopropanol. Thus, 2.82 g (87%) of the title compound are obtained. M.p.: 199°–203° C.

Step D
8-Chloro-4-methyl-1-(4-nitrophenyl)-4,5-dihydro-3H-2,3-benzodiazepine 1.62 g (5.16 mmoles) of the benzodiazepine derivative obtained in Step C are reduced according to the method described in Example 1, Step D. Thus, 1.59 g (98%) of the title compound are obtained. M.p.: 132° to 135° C.

EXAMPLE 6

3-Acetyl-1-(4-aminophenyl)-8-chloro-4-methyl-4,5-dihydro-3H-2,3-benzodiazepine 0.81 g (2.26 mmoles) of 3-acetyl-8-chloro-4-methyl-1-(4-nitrophenyl)-4,5-dihydro-3H-2,3-benzodiazepine obtained in Example 5 are reduced according to the method described in Example 2. The crude product is recrystallized from 50% aqueous ethanol to give 0.64 g (86%) of the title compound. M.p.: 187°–189° C.

EXAMPLE 7

8-Chloro-4-methyl-3-methylcarbamoyl-1-(4-nitrophenyl)-4,5-dihydro-3H-2,3-benzodiazepine Starting from 0.79 g (2.5 mmoles) of 8-chloro-4-methyl-1-(4-nitrophenyl)-4,5-dihydro-3H-2,3-benzodiazepine obtained in Example 5, Step D, the procedure of Example 3 is repeated. The crude product is recrystallized from isopropanol to obtain 0.85 g (91%) of the title compound. M.p.: 190°–192° C.

EXAMPLE 8

1-(4-Aminophenyl)-8-chloro-4-methyl-3-methylcarbamoyl-4,5-dihydro-3H-2,3-benzodiazepine 0.65 g (1.74 mmoles) of 8-chloro-4-methyl-3-methylcarbamoyl-1-(4-nitrophenyl)-4,5-dihydro-3H-2,3-benzodiazepine obtained in Example 7 are reduced according to the method described in Example 2. Thus, 0.59 g (99%) of the title compound are obtained. M.p.: 115°–118° C.

EXAMPLE 9

3-Acetyl-7,8-dichloro-4-methyl-1-(4-nitrophenyl)-4,5-dihydro-3H-2,3-benzodiazepine 0.35 g (0.99 mmoles) of 7,8-dichloro-4-methyl-1-(4-nitrophenyl)-4,5-dihydro-3H-2,3-benzodiazepine are acetylated by the method described in Example 1. Thus, 0.36 g (93%) of the title compound are obtained. M.p.: 198°–200° C.

The starting compound of Example 9 is prepared as follows:

Step A
6,7-Dichloro-3-methyl-1-(4-nitrophenyl)-isochroman

The procedure of Example 1, Step A is repeated with the exception that the starting compound consists of 10.47 g (51.0 mmoles) of 1-(3,4-dichlorophenyl)-2-propanol, and the reaction mixture is boiled for 3 hours. Thus, 4.29 g (25%) of the title compound are obtained. M.p.: 189°–191° C.

Step B
7,8-Dichloro-4-methyl-1-(4-nitrophenyl)-5H-2,3-benzodiazepine 4.75 g (14.0 mmoles) of the isochromane derivative prepared in Step A are oxidized according to the method of Example 1, Step B using Jones' reagent with the exception that instead of reacting the crude product with perchloric acid, the 1-acetonyl-3,4-dichloro-4'-nitrobenzophenone derivative (m.p.: 121°–122° C.) is isolated by chromatography. The solution of the above derivative in isopropanol is reacted with 98% hydrazine hydrate at 25° C. to obtain the monohydrazone derivative (m.p.: 167°–169° C.). The monohydrazone compound is reacted with methanol containing 15% hydrogen chloride, then, the hydrochloride of the title compound is treated with triethylamine to obtain the free base that is purified by recrystallization from hot dimethylformamide. M.p.: 231°–233° C.

Step C
7,8-Dichloro-4-methyl-1-(4-nitrophenyl)-4,5-dihydro-3H-2,3-benzodiazepine 0.74 g (2.1 mmoles) of the benzodiazepine derivative prepared in Step B are reduced using the method of Example 1, Step D. Thus, 0.70 g (95%) of the title compound are obtained. M.p.: 182°–184° C.

EXAMPLE 10

3-Acetyl-1-(4-aminophenyl)-7,8-dichloro-4-methyl-4,5-dihydro-3H-2,3-benzodiazepine 0.34 g (0.86 mmoles) of 3-acetyl-7,8-dichloro-4-methyl-1-(4-nitrophenyl)-4,5-dihydro-3H-2,3-benzodiazepine obtained in Example 9 are reduced using the method described in Example 2. The crude product is purified by suspending it in hot ethanol. Thus, 0.25 g (80%) of the title compound are obtained. M.p.: 242°–243° C.

EXAMPLE 11

7,8-Dichloro-4-methyl-3-methylcarbamoyl-1-(4-nitrophenyl)-4,5-dihydro-3H-2,3-benzodiazepine 0.33 g (0.94 mmoles) of 7,8-dichloro-4-methyl-1-(4-nitrophenyl)-4,5-dihydro-3H-2,3-benzodiazepine obtained in Example 9, Step C are reacted with methyl isocyanate according to Example 3. The crude product is purified by suspending it in hot ethanol. Thus, 0.37 g (97%) of the title compound are obtained. M.p.: 221°–223° C.

EXAMPLE 12

1-(4-Aminophenyl)-7,8-dichloro-4-methyl-3-methylcarbamoyl-4,5-dihydro-3H-2,3-benzodiazepine 0.35 g (0.85 mmoles) of 7,8-dichloro-4-methyl-3-methylcarbamoyl-1-(4-nitrophenyl)-4,5-dihydro-3H-2,3-benzodiazepine obtained in Example 11 are reduced using the method given in Example 2. The crude product is recrystallized from 50% aqueous ethanol. Thus, 0.27 g (84%) of the title compound are obtained. M.p.: 224°–225° C.

SUPPLEMENTARY EXAMPLES

EXAMPLE 13

3-Acetyl-8-chloro-4-methyl-1-(4-nitrophenyl)-4,5-dihydro-3H-2,3-benzodiazepine (The method of preparation is different from the one described in Example 5.)

6.35 g (about 16.3 mmoles) of crude acetic acid [1-/2-(2-hydroxypropyl)-5-chlorophenyl/-4-nitrophenyl methylene] hydrazide are dissolved in 70 ml of anhydrous dichloromethane, and the solution is cooled to −15° C. To the solution 4.10 ml (29.3 mmoles) of triethylamine are added under stirring, then 1.65 ml (21.2 mmoles) of mesyl chloride are added, drop by drop, in about 5 minutes. After 20 minutes, the reaction mixture is washed with 30 ml of ice cold 1N hydrochloric acid, then twice with ice acid aqueous sodium chloride solution using 30 ml of solution each time. The organic phase is dried and evaporated. The solid foamlike residue is suspended in 80 ml of ethanol, and 0.90 ml (17.1 mmoles) of 50% sodium hydroxide solution are added to the suspension, drop by drop, under ice cooling. The main part of the intermediate dissolves, and, after some minutes, yellow crystals begin to form. The mixture is stirred for further 4 hours, then 100 ml of water are added, drop by drop, under ice cooling in 45 minutes, the precipitate is filtered and washed with water.

The dry crude product is dissolved in about 450 ml of hot ethanol, and the solution is concentrated to about one third of its volume. After cooling, the solids are filtered to obtain 3.92 g of the title compound as yellow crystals. M.p.: 226°–228° C. (Yield: 67% calculated for the isochroman described in Example 5, Step A).

The starting compound of Example 13 is prepared as follows:

Step A
1-Hydroxy-7-chloro-3-methyl-1-(4-nitrophenyl)-isochroman 7.44 g (24.5 mmoles) of 7-chloro-3-methyl-1-(4-nitrophenyl)-isochromane (prepared as described in Example 5, Step A) are dissolved in a mixture of 50 ml of dimethylformamide and 24 ml of dimethyl sulfoxide, and the solution is cooled by ice water while introducing air through a capillary led under the surface of the liquid. Under vigorous bubbling, 2.60 ml (49.0 mmoles) of 50% aqueous sodium hydroxide solution are added to the reaction mixture that becomes violescent black. After 2 hours, the reaction mixture is poured onto 240 ml of ice cold 0.5N hydrochloric acid, and the flocculent precipitate is extracted 3 times using 100 ml of ethyl acetate each time. The combined organic solutions are washed with 100 ml of saturated aqueous sodium hydrogen carbonate solution and aqueous sodium chloride solution until neutrality, dried, and evaporated. 8.70 g of foam are obtained which consists of only one compound as shown by thin-layer chromatography ($R_F$=about 0.2 using a mixture of n-hexane and ethyl acetate in a ratio of 4:1).

On the basis of $^1$H NMR investigation, the compound consists of a mixture of two possible stereoisomers, and has a purity of about 90%.

The compound obtained is used for the further reaction step in the above form.

Step B
Acetic acid [1-/2-(2-hydroxypropyl)-5-chlorophenyl/-4-nitrophenylmethylene]hydrazide A mixture of 5.85 g (16.3 mmoles) of the hemiketal prepared in Step A (and having a purity of about 89 to 90%). 1.45 g (19.5 mmoles) of acetic hydrazide, 80 ml of isopropanol, 20 ml of water and 2 ml of 1N hydrochloric acid is boiled. In the beginning of boiling, the reagents dissolve. After 3.5 hours' boiling, further 0.33 g (4.45 mmoles) of acetic acid hydrazide and 1 ml of 1N hydrochloric acid are added to the mixture, and reacting is carried on for further 3.5 hours. Then, the reaction mixture is evaporated, and the residue is dissolved in a mixture of 150 ml of ethyl acetate and 100 ml of aqueous sodium hydrogen carbonate solution. After separation, the aqueous phase is extracted with further 50 ml of ethyl acetate, the combined organic solutions are washed with aqueous sodium chloride solution, dried, and evaporated. The water content of the foamlike residue is removed by adding and evaporating benzene, and the obtained 6.35 g of yellow gum is used in Example 13 for the mesylation and ring closure reaction.

EXAMPLE 14

3-Carbamoyl-8-chloro-4-methyl-1-(4-nitrophenyl)-4,5-dihydro-3H-2,3-benzodiazepine 6.13 g (about 16.27 mmoles) of crude 1-[/2-(2-hydroxypropyl)-5-chlorophenyl/-4-nitrophenylmethylene] semicarbazide are dissolved in 60 ml of anhydrous pyridine, and, to the solution obtained, 1.76 ml (22.77 mmoles) of mesyl chloride are added, drop by drop, under stirring, at –5° C. The reaction mixture is stirred at room temperature for 23 hours, then further 0.17 ml (2.8 mmoles) of mesyl chloride are added. After 3 hours, the mixture is poured onto 500 ml of 1.5N hydrochloric acid solution, and the product is extracted 3 times with dichloromethane using 90 ml of dichloromethane each time. The combined organic solutions are washed with aqueous sodium chloride solution, dried, and evaporated. The intermediate obtained as a solid foam is taken up in 100 ml of ethanol, and 1.03 ml (19.5 mmoles) of 50% aqueous sodium hydroxide solution are added to it, drop by drop, under stirring at room temperature. After 4 hours' stirring, 150 ml of water are added, drop by drop, to the reaction mixture under ice cooling, the crystalline product precipitated is filtered and washed with water.

The obtained 4.18 g (76%) of crude product are recrystallized by dissolving it in 270 ml of ethanol, and evaporating the solution to about one third of its original volume.

Thus, 3.16 g (54%) of the title compound are obtained. M.p.: 223°–234° C. (under decomposition).

The starting compound of Example 14 is prepared as follows:
1-[/2-(2-Hydroxypropyl)-5-chlorophenyl/-4-nitrophenylmethylene]semicarbazide 6.19 g (about 18 moles) of the hemiketal prepared as described in Example 13, Step A are reacted with 3.01 g (27 mmoles) of semicarbazide hydrochloride in a mixture of 140 ml of isopropanol and 60 ml of water. After 5 hours' boiling, further 0.60 g (5.4 mmoles) of semicarbazide hydrochloride are added to the reaction mixture that is boiled for further 5 hours. The mixture is evaporated, the residue is suspended in water, the product is filtered and washed with water.

6.62 g (98%) of the title compound are obtained which is used in the obtained form for the mesylation and ring closure reactions.

For analytical purpose, a sample was purified by column chromatography (silicagel, eluent: a mixture of chloroform and methanol in a ratio of 1:1). As evidenced by $^1$H NMR, the above sample consists of the stereoisomers in a ratio of about 1:1, and has a purity of about 90%. In mass spectrometry, M=376/378.

EXAMPLE 15

1-(4-Aminophenyl)-3-carbamoyl-8-chloro-4-methyl-4,5-dihydro-3H-2,3-benzodiazepine 3.16 g (8.81 mmoles) of 3-carbamoyl-8-chloro-4-methyl-I are salts formed with physiologically suitable inorganic or organic acids. A suitable inorganic acid is e.g. hydrochloric acid, hydrogen bromide, phosphoric acid or sulfuric acid. The organic acid is e.g. formic acid, acetic acid, maleic acid, fumaric acid, malic acid, lactic acid, tartaric acid, citric acid or methanesulfonic acid.

A preferred subgroup of the compounds of the invention consists of the compounds of the formula I, wherein $R^1$ represents an amino group in position 4, $R^2$, $R^4$ and $R^6$ stand for hydrogen, $R^5$ means a methyl group, $R^7$ is a halo and $R^3$ represents an aliphatic acyl group or an alkylcarbamoyl group.

Within this preferred subgroup, especially preferred species consist of the compounds wherein $R^3$ stands for an acetyl group, or propionyl group, a cyclopropylcarbonyl group or a methylcarbamoyl group.

The compounds of the invention can be prepared from the corresponding starting compounds of the formula II, wherein $R^1$, $R^2$, $R^4$, $R^5$, $R^6$ and $R^7$ are as defined above, by the analogy of the processes given in HU-P No. 206 719 or U.S. Pat. No. 5,459,137. The compounds of the formula I can be also prepared as follows: the suitably substituted isochroman derivative is oxidized by air to obtain a hemiketal that is reacted with an oxoreagent suitable for introducing the acyl group in position 3 (e.g. a carboxylic acid hydrazide, semicarbazide etc.), then, the benzodiazepine ring is formed by means of mesylation and alkaline ring closure.

Details of the preparation of the compounds of the formula I are shown by the Examples.

In the preferred preparation of the compounds of the invention, the useful methods of 2,3-benzodiazepine syntheses are employed. Thus, amino groups are alkylated with an alkyl halide or reductive amination with an oxo compound The starting compound of Example 16 is prepared as follows:

Ethyl 3-[/2-(2-hydroxypropyl)-5-chlorophenyl/-4-nitrophenylmethylene]carbazate 2.10 g (about 6 mmoles) of the hemiketal prepared according to Example 13, Step A are reacted with 1.25 g (12.0 mmoles) of ethyl carbazate in a mixture of 80 ml of ethanol and 60 ml of water containing 0.1 ml of concentrated hydrochloric acid under boiling. After 2 hours' boiling, further 0.12 g (1.2 mmoles) of ethyl carbazate and 1 drop of hydrochloric acid are added to the mixture that is boiled for further 2 hours. After evaporation, the residue is dissolved in aqueous sodium hydrogen carbonate solution, and crystalline product is filtered, and washed with water.

2.36 g (97%) of the title compound are obtained. The product is a mixture of the stereoisomers in a ratio of about 1:1. M.p.: 123°–125° C.

EXAMPLE 17

1-(4-Aminophenyl)-3-ethoxycarbonyl-8-chloro-4-methyl-4,5-dihydro-3H-2,3-benzodiazepine 1.93 g (4.97 mmoles) of 8-chloro-3-ethoxycarbonyl-4-methyl-1-(4-nitrophenyl)-4,5-dihydro-3H-2,3-benzodiazepine are reduced in a mixture of methanol and dichloromethane in a ratio of 4:1 in the presence of Raney nickel catalyst with hydrazine using the method described in Example 2. The product is purified by column chromatography (silicagel, eluent: a mixture of n-hexane and ethyl acetate in a rate of 1:1).

1.46 g (82%) of the title compound are obtained as a solid foam. M.p.: 95°–98° C.

EXAMPLE 18

3-n-Butylcarbamoyl-8-chloro-4-methyl-1-(4-nitrophenyl)-4,5-dihydro-3H-2,3-benzodiazepine 2.10 g (4.85 mmoles) of 1-[/3-chloro-6-(2-hydroxypropyl)/-4-nitrophenylmethylene]-4-n-butylsemicarbazide are acylated with 0.53 ml (6.79 mmoles) of mesyl chloride in dichloroethane in the presence of 1.22 ml (8.73 mmoles) of triethylamine according to the method described in Example 14. The crude intermediate is cyclized with 0.28 ml (5.33 mmoles) of 50% aqueous sodium hydroxide solution as described in Example 14. The 1.40 g of crude product obtained are recrystallized from methanol.

Thus, 1.14 g (56%) of the title compound are obtained. M.p.: 150° C.

The starting compound of Example 18 i.e. 1-[/3-chloro-6-(2-hydroxypropyl)/-4-nitrophenylmethylene]-4-n-butylsemicarbazide is prepared from 1hydroxy-7-chloro-3-methyl-1-(4-nitrophenyl)-isochroman (Example 13, Step A) and 4-n-butylsemicarbazide using the method described in connection with the starting substance of Example 14. The crude product separated as a gum is purified by column chromatography (silicagel, eluent: a mixture of hexane and ethyl acetate in a ratio of 1:1, $R_F$—about 0.2), then used in the process of Example 18.

EXAMPLE 19

1-(4-Aminophenyl)-3-n-butylcarbamoyl-8-chloro-4-methyl-4,5-dihydro-3H-2,3-benzodiazepine 1.14 g (2.75 mmoles) of 3-n-butylcarbamoyl-8-chloro-4-methyl-1-(4-nitrophenyl)-4,5-dihydro-3H-2,3-benzodiazepine (prepared as described in Example 18) are reduced with 0.70 ml (13.74 mmoles) of hydrazine hydrate in 90 ml of methanol in the presence of Raney nickel catalyst according to the method described in Example 2. The product is purified by column chromatography (silicagel, eluent: a mixture of dichloromethane and methanol in a ratio of 98:2). After evaporation, the product is isolated as a foam that can be powdered.

0.93 g (88%) of the title compound are obtained. M.p.: 89°–91° C.

EXAMPLE 20

3-Acetyl-7,8-dichloro-4-methyl-1-(4-nitrophenyl)-4,5-dihydro-3H-2,3-benzodiazepine (The method of preparation is different from the one described in Example 9)

6.26 g (about 15.3 mmoles) of crude acetic acid [1-/2-(2-hydroxypropyl)-4,5-dichlorophenyl/-4-nitrophenylmethylene]hydrazide (see Step B of this Example) are mesylated and cyclized by alkaline treatment according to Example 13.

Thus, 3.65 g (64% calculated for the isochroman described in Example 9, Step A) of the title compound are obtained as yellow crystals. M.p.: 190°–195° C.

The starting compound is prepared as follows:

Step A

1-Hydroxy-6,7-dichloro-3-methyl-1-(4-nitrophenyl) isochroman 6.0 g (17.7 mmoles) of 6,7-dichloro-3-methyl-1-(4-nitrophenyl)isochroman are oxidized using the method described in Example 13, Step A.

6.03 g (96%) of the title compound are isolated as yellow crystals. The crude product consisting of a mixture of the two possible stereoisomers is used in the next reaction step without further purification.

Step B

Acetic acid [/2-(2-hydroxypropyl)-4,5-dichlorophenyl-4-nitrophenylmethylene]hydrazide 5.18 g (14.6 mmoles) of the hemiketal prepared in Example 20, Step A) are reacted with acetic hydrazide using the method of Example 13, Step B. 6.26 g of the title compound are obtained as a yellow gum that is used in the mesylation and ring closure reactions.

EXAMPLE 21

7,8-Dichloro-4-methyl-3-methylcarbamoyl-1-(4-nitrophenyl)-4,5-dihydro-3H-2,3-benzodiazepine (The method of preparation is different from the one described in Example 11).

8.66 g (about 20.4 mmoles) of crude 1-[/3,4-dichloro-6-(2-hydroxypropyl)/-4-nitrophenylmethylene]-4-methylsemicarbazide are mesylated and cyclized according to the method described in Example 13. The crude product obtained is recrystallized from aqueous dimethylformamide.

Thus, 3.12 g (33% calculated for the isochroman described in Example 9, Step A) of the title compound are obtained as light yellow crystals. M.p.: 218°–220° C.

The starting compound i.e. 1-[/3,4-dichloro-6-(2-hydroxypropyl)-4-nitrophenylmethylene]-4-methylsemicarbazide is prepared from 1-hydroxy-6,7-dichloro-3-methyl-1-(4-nitrophenyl)isochroman (Example 20, Step A) and 4-methylsemicarbazide by a similar method as the one described in connection with the starting compound of Example 14. The crude product separated as a yellow gum is used in Example 21 without further purification.

EXAMPLE 22

3-Acetyl-8-bromo-4-methyl-1-(4-nitrophenyl)-4,5-dihydro-3H-2,3-benzodiazepine 0.82 g (2.28 mmoles) of 8-bromo-4-methyl-1-(4-nitrophenyl)-4,5-dihydro-3H-2,3-benzodiazepine are acylated according to the method of Example 1. Thus, 0.84 g (91%) of the title compound are obtained. M.p. 228°–230° C.

The starting compound of Example 22 is prepared as follows:

Step A
7-Bromo-3-methyl-1-(4-nitrophenyl)isochroman

The process of Example 1, Step A is repeated with the exception that 14.69 g (68.3 mmoles) of 1-(4-bromophenyl)-2-isopropanol /J. Med. Chem., 21, 454 (1978)/ are used by the starting compound. Thus, 10.94 g (46%) of the title compound are obtained. M.p.: 130°–133° C.

Step B
8-Bromo-3-methyl-1-(4-nitrophenyl)-2-benzopyrilium perchlorate 10.8 g (32.5 mmoles) of isochroman derivative prepared in Example 22, Step A are oxidized with Jones' reagent as described in Example 1, Step B. The product is prepared in glacial acetic acid with perchloric acid.

Thus, 4.91 g (34%) of the title compound are obtained. M.p.: 253°–256° C.

Step C
8-Bromo-4-methyl-1-(4-nitrophenyl)-5H-2,3-benzodiazepine 4.0 g (9.0 mmoles) of benzopyrilium perchlorate prepared in Example 22, Step B are treated with hydrazine hydrate according to the method of Example 1, Step C. Thus, 2.30 g (71%) of the title compound are obtained. M.p.: 200°–205° C.

Step D
8-Bromo-4-methyl-1-(4-nitrophenyl)-4,5-dihydro-3H-2,3-benzodiazepine 3.0 g (8.38 mmoles) of the benzodiazepine derivative prepared according to Example 22, Step C are reduced as described in Example 1, Step D. Thus, 2.79 g (92%) of the title compound are obtained. M.p.: 131°–135° C.

EXAMPLE 23

3-Acetyl-1-(4-aminophenyl)-8-bromo-4-methyl-4,5-dihydro-3H-2,3-benzodiazepine 0.80 g (2.0 mmoles) of 3-acetyl-8-bromo-4-methyl-1-(4-nitrophenyl)-4,5-dihydro-3H-2,3-benzodiazepine (prepared in Example 22) are reduced according to the method of Example 2. The crude product is crystallized from ethanol. Thus, 0.62 g (83%) of the title compound are obtained. M.p.: 205°–208° C.

EXAMPLE 24

8-Bromo-4-methyl-1-(4-nitrophenyl)-3-trifluoroacetyl-4,5-dihydro-3H-2,3-benzodiazepine 1.51 g (4.20 mmoles) of 8-bromo-4-methyl-1-(4-nitrophenyl)-4,5-dihydro-3H-2,3-benzodiazepine (prepared in Example 22, Step D) are stirred in a mixture of 5 ml of anhydrous dichloromethane and 5 ml of trifluoroacetic anhydride at 25° C. for 3 hours, then the reaction mixture is diluted with dichloromethane. The organic phase is washed with water and 2% aqueous sodium hydrogen carbonate solution, dried, and evaporated. The crude product is purified by suspending it in 5 ml of hot ethanol. After filtration and drying, 1.66 g (86%) of the title compound are obtained. M.p.: 193°–196° C.

EXAMPLE 25

1-(4-Aminophenyl)-8-bromo-4-methyl-3-trifluoroacetyl-4,5-dihydro-3H-2,3-benzodiazepine 1.64 g (3.60 mmoles) of 8-bromo-4-methyl-1-(4-nitrophenyl)-3-trifluoroacetyl-4,5-dihydro-3H-2,3-benzodiazepine (prepared in Example 24) are reduced according to the method of Example 2. The crude product is purified by chromatography over a silicagel column that is eluted with a mixture of chloroform and methanol in a ratio of 99:1.

Thus, 1.33 g (87%) of the title compound are obtained. M.p.: 93°–96° C.

EXAMPLE 26

8-Bromo-4-methyl-1-(4-nitrophenyl)-3-propionyl-4,5-dihydro-3H-2,3-benzodiazepine 1.33 g (3.7 mmoles) of 8-bromo-4-methyl-1-(4-nitrophenyl)-3-trifluoroacetyl-4,5-dihydro-3H-2,3-benzodiazepine (prepared in Example 22, Step D) are acylated with propionic anhydride using the method of Example 1. The crude product is purified by chromatography over a silicagel column that is eluted with a mixture of hexane and ethyl acetate in a ratio of 9:1. Thus, 1.07 g (70%) of the title compound are obtained. M.p.: 178°–180° C.

EXAMPLE 27

1-(4-Aminophenyl)-8bromo-4-methyl-3-propionyl-4,5-dihydro-3H-2,3-benzodiazepine 1.05 g (2.52 mmoles) of 8-bromo-4-methyl-1-(4-nitrophenyl)-3-propionyl-4,5-dihydro-3H-2,3-benzodiazepine (prepared in Example 26) are reduced according to the method of Example 2. The crude product is crystallized from ethanol. Thus, 0.85 g (87%) of the title compound are obtained. M.p.: 99°–102° C.

EXAMPLE 28

8-Bromo-3-cyclopropionyl-4-methyl-1-(4-nitrophenyl)-4,5-dihydro-3H-2,3-benzodiazepine 0.90 g (2.5 mmoles) of 8-bromo-4-methyl-1-(4-nitrophenyl)-4,5-dihydro-3H-2,3-benzodiazepine (prepared in Example 22, Step D) are acylated with 0.27 ml (3 mmoles) of cyclopropanecarbonyl chloride in 15 ml of anhydrous dichloromethane in the presence of 0.22 ml (3 mmoles) of triethylamine at 25° C. The reaction mixture is poured onto 25 g of crushed ice and extracted with dichloromethane. The organic phase is washed with water and aqueous sodium hydrogen carbonate solution, dried, and evaporated. The crude product is suspended in 3 ml of hot ethanol. After filtration and drying, 0.88 g (82%) of the title compound are obtained. M.p.: 172°–173° C.

EXAMPLE 29

1-(4-Aminophenyl)-8-bromo-3-cyclopropyl-4-methyl-4,5-dihydro-3H-2,3-benzodiazepine 0.76 g (1.77 mmoles) of 8-bromo-3-cyclopropionyl-4-methyl-1-(4-nitrophyenyl)-4,5-dihydro-3H-2,3-benzodiazepine (prepared in Example 28) are reduced according to the method of Example 2. The crude product is crystallized from a mixture of ethanol and hexane in a ratio of 1:4. Thus, 0.55 g (78%) of the title compound are obtained. M.p.: 113°–116° C.

EXAMPLE 30

8-Bromo-4-methyl-3-methylcarbamoyl-1-(4-nitrophenyl)-4,5-dihydro-3H-2,3-benzodiazepine 0.84 g (2.33 mmoles) of 8-bromo-4-methyl-1-(4-nitrophenyl)-4,5-dihydro-3H-2,3-benzodiazepine (prepared in Example 22, Step D) are reacted with methyl isocyanate according to the method of Example 3. The crude product is suspended in 5 ml of hot ethanol. After filtration and drying, 0.82 g (84%) of the title compound are obtained. M.p.: 197°–200° C.

EXAMPLE 31

1-(4-Aminophenyl)-8-bromo-4-methyl-3-methylcarbamoyl-4,5-dihydro-3H-2,3-benzodiazepine 0.80 g (1.92 mmoles) of 8-bromo-4-methyl-3-methylcarbamoyl-1-(4-nitrophenyl)-4,5-dihydro-3H-2,3-benzodiazepine (prepared in Example 30) are reduced according to the method of Example 2. The crude product is crystallized from 3 ml of ethyl acetate. Thus, 0.50 g (68%) of the title compound are obtained. M.p.: 121°–124° C.

EXAMPLE 32

8-Bromo-3-ethoxycarbonyl-4-methyl-1-(4-nitrophenyl)-4,5-dihydro-3H-2,3-benzodiazepine 8.11 g (18 mmoles) of ethyl 3-[/5-bromo-2-(2-hydroxypropyl)phenyl/-4-nitrophenylmethylene]-carbazate are reacted with mesyl chloride, then with 50% aqueous sodium hydroxide solution according to the method described in Example 16. The product is extracted with dichloro-methane, the organic phase is washed with water, dried, and evaporated. 6.78 g (87%) of the title compound are obtained as a solid foam that is used in this form in Example 33.

The starting compound is prepared as follows:
Step A
7-Bromo-1-hydroxy-3-methyl-1-(4-nitrophenyl)isochroman
15.56 g (44.7 mmoles) of 7-bromo-1-hydroxy-3-methyl-1-(4-nitrophenyl)isochroman (prepared in Example 22, Step A) are oxidized using the method described in Example 13, Step A. The product is extracted with benzene, dried, and evaporated. Thus, 14.80 g (91%) of the title compound are obtained that is a mixture of the possible isomers. The product is used without any further purification.

Step B
Ethyl 3-[/5-bromo-2-(2-hydroxypropyl)phenyl/-4-nitrophenylmethylene]carbazate
6.82 g (18.72 mmoles) of the hemiketal derivative prepared in Example 32, Step A are reacted with ethyl carbazate using the method described in connection with the preparation of the starting compound of Example 16. The product is extracted with ethyl acetate, the organic phase is washed with water, dried, and evaporated.

Thus, 8.11 g (96%) of the title compound are obtained. The product consisting of a mixture of the possible isomers is used without any further purification.

EXAMPLE 33

1-(4-Aminophenyl)-8-bromo-3-ethoxycarbonyl-4-methyl-4,5-dihydro-3H-2,3-benzodiazepine 1.58 g (3.66 mmoles) of 8-bromo-3-ethoxycarbonyl-4-methyl-1-(4-nitrophenyl)-4,5-dihydro-3H-2,3-benzodiazepine (prepared in Example 32) are reduced according to the method described in Example 2. The crude product is crystallized from 4 ml of ethyl acetate. Thus, 1.20 g (81%) of the title compound are obtained. M.p.: 114°–117° C.

EXAMPLE 34

8-Bromo-3-carbamoyl-4-methyl-1-(4-nitrophenyl)-4,5-dihydro-3H-2,3-benzodiazepine A solution of 1.80 g (5 mmoles) of 8-bromo-4-methyl-1-(4-nitrophenyl)-4,5-dihydro-3H-2,3-benzodiazepine in 10 ml of glacial acetic acid is treated with 0.53 g (6.5 mmoles) of potassium cyanate. After 1 hour, the solution is poured onto water, and the precipitated crystals are filtered. The crude product is suspended in 15 ml of hot ethanol. After filtration and drying, 1.56 g (77%) of the title compound are obtained. M.p.: 193°–203° C.

The starting compound of Example 34 is prepared as follows:
8-Bromo-4-methyl-1-(4-nitrophenyl)-4,5-dihydro-3H-2,3-benzodiazepine
(The compound is identical with the product of Example 22, Step D.)
5.20 g (12 mmoles) of 8-bromo-3-ethoxycarbonyl-4-methyl-1-(4-nitrophenyl)-4,5-dihydro-3H-2,3-benzodiazepine (prepared in Example 32) are boiled in 104 ml of methanol with 6 ml of 10N sodium hydroxide solution for 2 hours. After cooling, the reaction mixture is diluted with 104 ml of water, and the precipitated crystals are filtered. Thus, 3.99 g (92%) of the title compound are obtained. M.p.: 125°–130° C.

EXAMPLE 35

1-(4-Aminophenyl)-8-bromo-3-carbamoyl-4-methyl-4,5-dihydro-3H-2,3-benzodiazepine 1.55 g (3.84 mmoles) of 8-bromo-3-carbamoyl-4-methyl-1-(4-nitrophenyl)-4,5-dihydro-3H-2,3-benzodiazepine (prepared in Example 34) are reduced using the method of Example 2. The crude product is crystallized from 5 ml of ethanol. Thus, 1.19 g (83%) of the title compound are obtained. M.p.: 218°–221° C.

EXAMPLE 36

8-Chloro-4-methyl-1-(4-nitrophenyl)-3-trifluoroacetyl-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D) are acylated with trifluoroacetic anhydride according to the method of Example 24. 0.76 g (97%) of the title compound are obtained. M.p.: 150°–152° C.

The starting compound is identical with the product of Example 5, Step D, however, it can be also prepared as follows:

10.98 g (27 mmoles) of 3-ethoxycarbonyl-8-chloro-4-methyl-1-(4-nitrophenyl)-4,5-dihydro-3H-2,3-benzodiazepine (prepared in Example 16) are hydrolyzed using the method described in connection with the preparation of the starting compound of Example 34.

Thus, 8.04 g (94%) of the title compound are obtained. M.p.: 146°–151° C.

EXAMPLE 37

1-(4-Aminophenyl)-8-chloro-4-methyl-3-trifluoroacetyl-4,5-dihydro-3H-2,3-benzodiazepine 0.75 g (1.8 mmoles) of 8-chloro-4-methyl-1-(4-nitrophenyl)-3-trifluoroacetyl-4,5-dihydro-3H-2,3-benzodiazepine (prepared in Example 36) are reduced according to the method of Example 2. The crude product is purified by chromatography over a silicagel column that is eluted with a mixture of benzene and ethyl acetate in a ratio of 8:1. Thus, 0.47 g (68%) of the title compound are obtained. M.p.: 165°–167° C.

EXAMPLE 38

8-Chloro-4-methyl-1-(4-nitrophenyl)-3-propionyl-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D or in Example 36, starting compound) are acylated with propionic anhydride according to the method of Example 26. The crude product is purified by chromatography over a silicagel column that is eluted with a mixture of benzene and ethyl acetate in a ratio of 95:5. Thus, 0.96 g (79%) of the title compound are obtained. M.p.: 160°–161° C.

EXAMPLE 39

1-(4-Aminophenyl)-8-chloro-4-methyl-3-propionyl-4,5-dihydro-3H-2,3-benzodiazepine 0.46 g (1.23 mmoles) of 8-chloro-4-methyl-1-(4-nitrophenyl)-3-propionyl-4,5-dihydro-3H-2,3-benzodiazepine (prepared in Example 38) are reduced according to the method of Example 2. The crude product is crystallized from 50% aqueous ethanol. Thus, 0.39 g (93%) of the title compound are obtained. M.p.: 118°–120° C.

EXAMPLE 40

3-Cyclopropionyl-8-chloro-4-methyl-1-(4-nitrophenyl)-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D or in Example 36, starting substance) are acylated with cyclopropanecarbonyl chloride according to the method of Example 28. 0.71 g (97%) of the title compound are obtained. M.p.: 158°–160° C.

EXAMPLE 41

1-(4-Aminophenyl)-3-cyclopropionyl-8-chloro-4-methyl-4,5-dihydro-3H-2,3-benzodiazepine 0.72 g (1.87 mmoles) of 3-cyclopropionyl-8-chloro-4-methyl-1-(4-nitrophenyl)-4,5-dihydro-3H-2,3-benzodiazepine (prepared in Example 40) are reduced according to the method of Example 2. The crude product is recrystallized from 50% aqueous ethanol. Thus, 0.57 g (86%) of the title compound are obtained. M.p.: 122°–124° C.

EXAMPLE 42

(+)-3-Acetyl-8-chloro-4-methyl-1-(4-nitrophenyl)-4,5-dihydro-5H-2,3-benzodiazepine 0.51 g (1.6 mmoles) of (+)-8-chloro-4-methyl-1-(4-nitrophenyl)-4,5-dihydro-5H-2,3-benzodiazepine are acylated with acetic anhydride according to the method of Example 1. The 0.54 g of crude product are crystallized from 28 ml of ethyl acetate at room temperature. Thus, 0.28 g (48%) of the title compound are obtained. M.p.: 259°–260° C. On basis of chiral HLPC investigation (Chiralcel OJ, eluent: a mixture of hexane and ethanol in a ratio of 1:1) the product consists of one isomer.

The starting compound of Example 42 is prepared as follows:
(+)-8-Chloro-4-methyl-1-(4-nitrophenyl)-4,5-dihydro-5H-2,3-benzodiazepine To a solution of 6.03 g (23.6 mmoles) of R-(+)-2-amino-1,1-diphenyl-3-methylbutane-1-ol /J. Org. Chem., 49, 555 (1984); J. Chem. Soc. Perkin. Trans. I. 2039 (1985)/ in 60 ml of anhydrous dichloroethane, 2.43 ml (21.5 mmoles) of borane-dimethyl sulfide complex (concentration of borane: about 9.2M) are added, drop by drop, at −20° C. In 3 hours, the temperature of the solution is allowed to rise to 0° C., and the solution is held at +4° C. for 15 hours. To the thus-obtained solution of reducing complex, a solution of 3.37 g (10.7 mmoles) of 8-chloro-4-methyl-1-(4-nitrophenyl)-4,5-dihydro-5H-2,3-benzodiazepine (prepared in Example 5, Step C) in 60 ml of anhydrous dichloromethane are added, drop by drop, at room temperature during 30 minutes. The reaction mixture is stirred at 60° C. for 6 hours. The orange solution is cooled to 25° C., treated with 50 ml of 10% aqueous sodium carbonate solution, washed with water until neutrality, then dried, and evaporated. The product is separated over a silicagel column using a mixture of benzene and ethyl acetate in a ratio of 8:1.

The title compound obtained consists of a mixture of the enantiomers in a ratio of 75:25 (HPLC: Chiralcel OJ, eluent: a mixture of hexane and ethanol in a ratio of 1:1).

EXAMPLE 43

(−)-3-Acetyl-1-(4-aminophenyl)-8-chloro-4-methyl-4,5-dihydro-5H-2,3-benzodiazepine 0.28 g (0.78 mmoles) of (+)-3-acetyl-8-chloro-4-methyl-1-(4-nitrophenyl)-4,5-dihydro-5H-2,3-benzodiazepine (prepared in Example 42) are reduced according to the method of Example 2. The crude product is crystallized from 2 ml of ethanol. Thus, 0.15 g (58%) of the title compound are obtained. M.p.: 219°–220° C. $[\alpha]_D^{25}=-712.1$ (c=0.7; chloroform). The product consists of one enantiomer (HPLC: Chiralcel OJ, eluent: a mixture of hexane and ethanol in a ratio of 1:1).

EXAMPLE 44

3-(Ethylcarbamoyl)-8-chloro-4-methyl-1-(4-nitrophenyl)-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D or in Example 36, starting compound) are boiled with 0.75 ml (9.5 mmoles) of ethyl isocyanate in 25 ml of anhydrous toluene for 24 hours. The mixture is evaporated, the residue is recrystallized from 5 ml of ethanol. Thus, 0.51 g (69%) of the title compound are obtained. M.p.: 170°–172° C.

EXAMPLE 45

1-(4-Aminophenyl)-3-(ethylcarbamoyl)-8-chloro-4-methyl-4,5-dihydro-3H-2,3-benzodiazepine 0.48 g (1.24 mmoles) of 8-chloro-3-(ethylcarbamoyl)-4-methyl-1-(4-nitrophenyl)-4,5-dihydro-3H-2,3-benzodiazepine (prepared in Example 44) are reduced according to the method of Example 2. The crude product is recrystallized from 4 ml of 50% aqueous ethanol. Thus, 0.35 g (79%) of the title compound are obtained. M.p.: 165°–167° C.

EXAMPLE 46

8-Chloro-4-methyl-1-(4-nitrophenyl)-3-(n-propylcarbamoyl)-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D or in Example 36, starting compound) are reacted with n-propyl isocyanate according to the method described in Example 44. The crude product is recrystallized from ethanol. Thus, 0.63 g (83%) of the title compound are obtained. M.p.: 186°–187° C.

EXAMPLE 47

1-(4-Aminophenyl)-8-chloro-4-methyl-3-(n-propylcarbamoyl)-4,5-dihydro-3H-2,3-benzodiazepine 0.6 g (1.5 mmoles) of 8-chloro-4-methyl-1-(4-nitrophenyl)-3-(n-propylcarbamoyl)-4,5-dihydro-3H-2,3-benzodiazepine (prepared in Example 46) are reduced according to the method of Example 2. Thus, 0.52 g (93%) of the title compound are obtained. M.p.: 88°–90° C.

EXAMPLE 48

3-(Isopropylcarbamoyl)-8-chloro-4-methyl-1-(4-nitrophenyl)-4,5-dihydro-3H-2,3-benzodiazepine 0.6 g (1.9 mmoles) of 8-chloro-4-methyl-1-(4-nitrophenyl)-4,5-dihydro-3H-2,3-benzodiazepine (prepared in Example 5, Step D or in Example 36, starting compound) are reacted with isopropyl isocyanate according to the method of Example 44. The crude product is recrystallized from ethanol. Thus, 0.4 g (53%) of the title compound are obtained. M.p.: 172°–174° C.

EXAMPLE 49

1-(4-Aminophenyl)-3-(isopropylcarbamoyl)-8-chloro-4-methyl-4,5-dihydro-3H-2,3-benzodiazepine 0.38 g (0.95 mmoles) of 3-(isopropylcarbamoyl)-8-chloro-4-methyl-1-(4-nitrophenyl)-4,5-dihydro-3H-2,3-benzodiazepine (prepared in Example 48) are reduced according to the method of Example 2. Thus, 0.32 g (91%) of the title compound are obtained. M.p.: 100°–102° C.

EXAMPLE 50

3-Ethoxycarbonyl-7,8-dichloro-4-methyl-1-(4-nitrophenyl)-4,5-dihydro-3H-2,3-benzodiazepine 1.41 g (about 2.7 mmoles) of crude ethyl 3-[/2-(2-hydroxypropyl)-4,5-dichlorophenyl/-4-nitrophenylmethylene]-carbazate are mesylated and cyclized as described in Example 13. Thus, 0.94 g (75% calculated for the isochroman described in Example 9, Step A) of the title compound are obtained. M.p.: 106°–108° C.

The starting compound of Example 50 is prepared as follows:
Ethyl 3-[/2-(2-hydroxypropyl)-4,5-dichlorophenyl/-4-nitrophenylmethylene]-carbazate
0.98 g (2.8 mmoles) of 1-hydroxy-6,7-dichloro-3-methyl-1-(4-nitrophenyl)isochroman (prepared in Example 20, Step A) are reacted with ethyl carbazate according to the method described in connection with the preparation of the starting compound of Example 16. Thus, 1.20 g (97%) of the title compound are obtained consisting of a mixture of the possible isomers. The product is used without any further purification.

EXAMPLE 51

1-(4-Aminophenyl)-3-ethoxycarbonyl-7,8-dichloro-4-methyl-4,5-dihydro-3H-2,3-benzodiazepine 0.94 g (2.2 mmoles) of 3-ethoxycarbonyl-7,8-dichloro-4-methyl-1-(4-nitrophenyl)-4,5-dihydro-3H-2,3-benzodiazepine (prepared in Example 50) are reduced according to the method of Example 2. The crude product is purified by chromatography over a silicagel column that is eluted with a mixture of benzene and ethyl acetate in a ratio of 4:1. Then, the product is recrystallized from ethanol.

Thus, 0.54 g (63%) of the title compound are obtained. M.p.: 190°–192° C.

EXAMPLE 52

3-Butyryl-7,8-dichloro-4-methyl-1-(4-nitrophenyl)-4,5-dihydro-3H-2,3-benzodiazepine 1.31 g (about 3 mmoles) of crude butyric-[1-/2-(2-hydroxypropyl)-4,5-dichlorophenyl/-4-nitrophenylmethylene]-hydrazide are mesylated and cyclized according to the method of Example 13. Thus, 1.08 g (86% calculated for the isochroman described in Example 9, Step A) of the title compound are obtained. M.p.: 75°–77° C. The starting compound of Example 52 is prepared as follows:
Butyric-[1-/2-(2-hydroxypropyl)-4,5-dichlorophenyl/-4-nitrophenylmethylene]-hydrazide
1.06 g (3 mmoles) of the hemiketal prepared in Example 20, Step A are reacted with butyric hydrazide according to the method of Example 13, Step B. 1.31 g of the title compound are obtained as a yellow amorphous substance that is used without any further purification for the mesylation and ring closure reactions.

EXAMPLE 53

1-(4-Aminophenyl)-3-butyryl-7,8-dichloro-4-methyl-4,5-dihydro-3H-2,3-benzodiazepine 1.08 g (2.6 mmoles) of 3-butyryl-7,8-dichloro-4-methyl-1-(4-nitrophenyl)-4,5-dihydro-3H-2,3-benzodiazepine (prepared in Example 52) are reduced according to the method described in Example 2. The crude product is purified by chromatography over a silicagel column that is eluted with a mixture of benzene and ethyl acetate in a ratio of 8:1. Then, the product is suspended in hot ethanol.

Thus, 0.57 g (57%) of the title compound are obtained. M.p.: 193°–194° C.

Using the methods of the above Examples the following compounds are prepared:

7,8-dichloro-4-methyl-1-(4-nitrophenyl)-3-propionyl-4,5-dihydro-3H-2,3-benzodiazepine, 1-(4-aminophenyl)-7,8-dichloro-4-methyl-3-propionyl-4,5-dihydro-3H-2,3-benzodiazepine, 3-carbamoyl-7,8-dichloro-4-methyl-1-(4-nitrophenyl)-4,5-dihydro-3H-2,3-benzodiazepine, 1-(4-aminophenyl)-3-carbamoyl-7,8-dichloro-4-methyl-4,5-dihydro-3H-2,3-benzodiazepine.

We claim:

1. A compound of the formula I

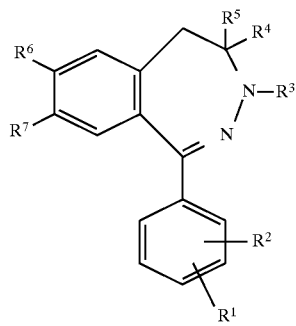

wherein $R^1$ and $R^2$ represent, independently, a hydrogen, a halogen, a $C_{1-4}$ alkyl group, a $C_{1-4}$ alkoxy group, a nitro group, a trifluoromethyl group or a group of the formula —$NR^8R^9$, wherein $R^8$ and $R^9$ represent, independently, a hydrogen, a $C_{1-4}$ alkyl group or a group of the formula —$COR^{10}$, wherein $R^{10}$ is a hydrogen, a $C_{1-6}$ alkyl group that can be substituted, a $C_{6-10}$ aryl group, a $C_{1-4}$ alkoxy group, a $C_{3-5}$ cycloalkyl group, a $C_{2-6}$ alkenyl group, a $C_{3-5}$ cyclo-alkoxy group or a group of the formula —$NR^{11}R^{12}$, wherein $R^{11}$ and $R^{12}$ represent, independently, a hydrogen, a $C_{1-4}$ alkyl group, a $C_{3-5}$ cycloalkyl group or a $C_{6-10}$ aryl group, wherein $R^3$ represents a $C_{1-4}$ alkyl group, a $C_{3-5}$ cycloalkyl group or a group of the formula —CO—$R^{13}$, wherein $R^{13}$ has the same definitions given in relation to $R^{10}$, wherein $R^4$ and $R^5$ represent, independently, a hydrogen or a $C_{1-3}$ alkyl group, wherein $R^6$ and $R^7$, are, independently, a hydrogen, a chloro or a bromo, wherein $R^6$ and $R^7$ are not both hydrogen, and the isomers of said compound and acid addition salts of said compound and of said isomers.

2. A compound which is 3-Acetyl-1-(4-aminophenyl)-8-chloro-4-methyl-4,5-dihydro-3H-2,3-benzodiazepine.

3. A compound which is 1-(4-Aminophenyl)-8-chloro-4-methyl-3-methyl-carbamoyl-4,5-dihydro-3H-2,3-benzodiazepine.

4. A pharmaceutical composition comprising a compound of the formula I

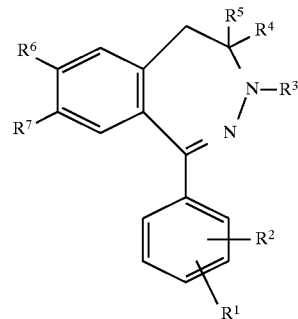

wherein $R^1$ to $R^7$ are as defined in claim 1, or an isomer of said compound or a pharmaceutically acceptable acid addition salt of said compound or said isomer.

5. A pharmaceutical composition comprising the compound as defined in claim 4, and further comprising at least one member selected from the group consisting of conventional carriers, solvents, diluents and excipients used in the preparation of pharmaceutical compositions.

6. A method of treating diseases accompanied by muscle spasticity comprising administering to a mammal in need thereof an effective amount of the compound defined in claim 1.

7. A method of treating epilepsy comprising administering to a mammal in need thereof an effective amount of the compound defined in claim 1.

8. A method of treating acute or chronic neurodegenerative diseases comprising administering to a mammal in need thereof an effective amount of the compound defined in claim 1.

9. A process for the preparation of compounds of formula I

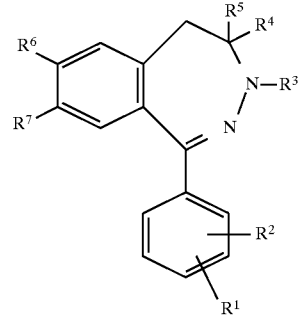

wherein $R^1$, $R^2$, $R^3$, $R^4$, $R^5$, $R^6$, and $R^7$ have the same meaning as in claim 1, and the isomers of said compound and acid addition salts of said compound, comprising introducing the $R^3$ group into position 3 of a compound of formula II

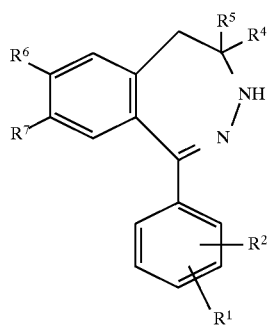

Formula II wherein $R^1$, $R^2$, $R^4$, $R^5$, $R^6$, and $R^7$ are as stated above, and, optionally converting a compound of the formula I into an acid addition salt of said compound or setting free said compound of the formula I from an acid addition salt.

10. A compound of formula II

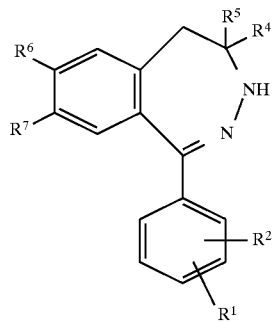

wherein $R^1$ and $R^2$ represent, independently, a hydrogen, a halogen, a $C_{1-4}$ alkyl group, a $C_{1-4}$ alkoxy group, a nitro group, a trifluoromethyl group or a group of the formula —$NR^8R^9$, wherein $R^8$ and $R^9$ represent, independently, a hydrogen, a $C_{1-4}$ alkyl group or a group of the formula —$COR^{10}$, wherein $R^{10}$ is a hydrogen, a $C_{1-6}$ alkyl group that can be substituted, a $C_{6-10}$ aryl group, a $C_{1-4}$ alkoxy group, a $C_{3-5}$ cycloalkyl group, a $C_{2-6}$ alkenyl group, a $C_{3-5}$ cyclo-alkoxy group or a group of the formula —$NR^{11}R^{12}$, wherein $R^{11}$ and $R^{12}$ represent, independently, a hydrogen, a $C_{1-4}$ alkyl group, a $C_{3-5}$ cycloalkyl group or a $C_{6-10}$ aryl group, wherein $R^3$ represents a hydrogen, wherein $R^4$ and $R^5$ represent, independently, a hydrogen or a $C_{1-3}$ alkyl group, wherein $R^6$ and $R^7$ are, independently, a hydrogen, a chloro or a bromo, wherein $R^6$ and $R^7$ are not both hydrogen.

11. A method of non-competitively antagonizing an amino acid receptor comprising administering to a mammal in need thereof an effective amount of the compound defined in claim 1.

12. The method as defined in claim 11 wherein the amino acid receptor is an AMPA receptor.

* * * * *